United States Patent [19]
Barshad

[11] Patent Number: 5,621,213
[45] Date of Patent: Apr. 15, 1997

[54] SYSTEM AND METHOD FOR MONITORING A STACK GAS

[75] Inventor: Yoav Barshad, Brookline, Mass.

[73] Assignee: Novitron International Inc., Newton, Mass.

[21] Appl. No.: 499,806

[22] Filed: Jul. 7, 1995

[51] Int. Cl.[6] ................................. G01J 3/32; G01J 3/42
[52] U.S. Cl. ...................... 250/373; 250/252.1; 250/372; 250/343; 250/339.05; 250/339.03; 356/437; 356/438; 356/439; 423/235
[58] Field of Search ............................... 250/373, 252.1, 250/372, 343, 339.05, 339.03; 356/437, 438, 439; 423/235

[56] References Cited

U.S. PATENT DOCUMENTS

| | | |
|---|---|---|
| 3,979,589 | 9/1976 | Sternberg et al. . |
| 4,126,396 | 11/1978 | Hartmann et al. . |
| 4,441,815 | 4/1984 | Izumi . |
| 4,736,103 | 4/1988 | Nelson et al. ........................ 250/343 |
| 5,053,623 | 10/1991 | McGowan et al. . |
| 5,078,973 | 1/1992 | Kuroda et al. ........................ 423/235 |
| 5,272,345 | 12/1993 | Durham et al. . |
| 5,304,362 | 4/1994 | Madsen ................................ 423/235 |

FOREIGN PATENT DOCUMENTS

| | | |
|---|---|---|
| 0591758 | 4/1994 | European Pat. Off. . |
| 3-65217 | 3/1991 | Japan .................................... 423/235 |

Primary Examiner—Michael J. Tokar
Assistant Examiner—Virgil O. Tyler
Attorney, Agent, or Firm—M. LuKacher

[57] ABSTRACT

A stack gas monitor system has an optimized gas flow portion which is permanently installed in a fossil fuel burning facility, and to which a spectrophotometric portion can be readily coupled for real-time determination in the system of a concentration of a first gas having a characteristic absorption spectrum and which is selectably introducible as a measured amount into a stack gas stream. A sample of the stack gas stream is flowing through the gas flow portion, with at least one gas of the sample stream having an absorption spectrum extending within an ultraviolet range of wavelengths of radiation and having absorbance values within this range which are higher than absorbance values of the first gas. The system can be purged and can be calibrated with the first gas. Stack gas blank data are obtained in the absence of the first gas. Composite gas data are provided upon introduction of the first gas into the stack gas. Absorbance values for the first gas in the composite gas are calculated, and first gas concentration levels are determined and are monitored on a periodic basis.

24 Claims, 3 Drawing Sheets

SYSTEM AND METHOD FOR MONITORING A STACK GAS

FIELD OF THE INVENTION

The present invention generally relates to the monitoring of a stack gas, and more particularly, the invention relates to a system and method for real-time spectrophotometric determination of a concentration of a first gas having a characteristic absorption spectrum and which is selectably introducible as a measured amount into a stack gas-stream of a plurality of stack gases glowing as a sample gas stream through a gas flow portion of the system with at least one gas of the stack gas stream having an absorption spectrum extending within an ultraviolet range of wavelengths of radiation and having absorbance values in this spectral range which are higher than absorbance values of the first gas when introduced into the stack gas steam to form a composite gas stream.

BACKGROUND OF THE INVENTION

Due to growing environmental awareness and increasing regulation governing the emission from exhaust stacks, particularly of power generating plants using coal-fired burning facilities, numerous efforts have been made to firstly detect the various components of a stack gas stream and to secondly address the transformation of some of these components into gases having a reduced adverse environmental impact. With respect to detecting individual component gases in a stack gas stream, spectrophotometric approaches have been developed since spectrophotometric analysis of a plurality of gases provides, at least in principle, for relatively precise determination of individual gases in a stack gas stream, with each of the component gases having in its pure or isolated from a characteristic absorption spectrum. Thus, it has been possible to detect with suitably designed spectrophotometers a concentration of a trace amount of one gas present in a larger amount of another gas, where the other gas has a characteristic absorption spectrum which substantially overlaps a characteristic absorption spectrum of the trace gas.

The design and operation of spectrophotometers per se, and of spectrophotometers adapted for use in gas analysis, are well known. Such known spectrophotometers, also referred to as spectrometers or spectral analyzers, will be described briefly hereinafter in conjunction with considerations of requirements for providing gas samples representative of the stack gases in an operative environment of a power plant such that the samples can be characterized spectrophotometrically under conditions which most closely resemble the composition of the gases in the stack. ideally, in such an environment of an operating plant, various conduits and associated valves, flow regulators, and a gas flow-through chamber for optical analysis of stack gas samples would be provided during the initial construction of the plant or would be provided during an upgrade thereof. A spectrophotometer, preferably of a readily transportable type without moving parts therein, could then be brought to each plant so equipped, optically coupled into the pre-installed flow-through chamber, and deployed to determine concentration levels of gases to be monitored on a periodic basis, for example on a monthly basis.

A stack gas stream, particularly a stack gas stream from a coal-fired facility, typically includes numerous gases, such as, for example, CO, $CO_2$, NO, $NO_2$, $SO_2$, and water vapor, with each of these gases having substantially differing levels of concentration and having differing characteristic absorption spectra. Additionally, stack gases entering a stack frequently are at a temperature of approximately 300° C.

When it is necessary to reduce the concentrations of the nitrogen oxide gases (NO, $NO_2$) in the stack gas stream, a reactive gas, for example, $NH_3$, is added to the stack gas stream at or near the base of the stack so as to react with the nitrogen oxide constituents of the stack gas and thereby forming through a chemical reaction molecular nitrogen ($N_2$) and water vapor, such transformed compounds being environmentally significantly more benign than the nitrogen oxides and the $NH_3$ addition gas. It has been found in the operation of fossil fuel-fired facilities that it is advantageous to add a slight excess of the $NH_3$ reactive gas over the amount required to transform the nitrogen oxides into molecular nitrogen and water vapor and to spectrophotometrically monitor the concentration of this slight excess of $NH_3$ in a sample of the remaining stack gases, rather than to monitor the concentration of the molecular nitrogen and water vapor.

While $NH_3$ has a characteristic absorption spectrum in an ultraviolet spectral region of wavelengths, so does unfortunately the $SO_2$ constituent of the stack gas stream. Since the concentration of $SO_2$ in the stack gas stream can be in the range of 2,000 parts per million (ppm) depending on the type of fuel being burned, the concentration of the residual or trace quantity of $NH_3$ being kept to a minimum level frequently in the range of from 2–10 ppm. Accordingly, at a selected gas flow rate of a sample through a gas flow-through chamber having particular dimensions, a spectrophotometric measurement in an ultraviolet spectral region can, for example, indicate an absorbance value of 1.0 for $SO_2$, and an absorbance value of 0.10 or less for the residual $NH_3$ constituent, with both measurements performed at a particular wavelength, for example, at a wavelength of 200 nm. Thus, in order to reliably detect low concentrations of $NH_3$ in a gas stream having a plurality of gases, including $SO_2$ at relatively high concentration levels, it becomes imperative to devise a stack gas monitor system which provides the capability to conduct such measurements at a periodic basis with relative ease in the operating environment of an industrial or commercial facility.

It is also known that when the temperature of the flow-through chamber or measuring chamber and the conduits leading to and from the chamber is allowed to decrease to a temperature lower than about 250° C., a chemical reaction between the $SO_2$ and the $NH_3$ can commence, thereby forming an ammonium sulfate deposit, and more specifically an ammonium bisulfate deposit, within the conduits and the measuring chamber. Such formation of ammonium sulfate not only reduces the measured concentration of ammonium gas ($NH_3$) in the flow-through chamber by that reaction, but can also lead to a relatively rapid buildup of deposits within the inner walls of the conduits and within the measuring chamber thereby necessitating either time-consuming and expensive cleanout procedures during which the gas flow of the sample gas stream has to be suspended, or in a worst case, requiring the operation of the burner facility of the plant to be disrupted. Accordingly, it is important to prevent or at least to minimize the buildup of such ammonium sulfate deposits by ensuring that the temperature of at least a conduit extending between the stack and a flow-through measuring chamber, the temperature of the chamber, and preferably the temperature of a conduit extending between the chamber and a gas flow monitor system is maintained at about 300° C., which is a temperature comparable to the temperature of the stack gas stream entering the stack.

When it is required to reliably detect a concentration of a first gas which is present at relatively low concentration in a second gas, and both gases have substantially overlapping characteristic absorption spectra, it has been recognized in the art of spectrophotometric analysis of gas mixtures that a gas concentration calibration is desirable for at least the one gas having the lower or trace concentration and also having lower absorbance values compared to the second gas over the same spectral region.

It has also been appreciated in the art of spectrophotometric gas analysis to establish a spectrophotometric reference level which can be a so-called blanking level corresponding to a spectrophotometric determination of the spectral absorbance of a measuring chamber in either the absence of any absorbing gas, such as would prevail if the chamber were to be evacuated, or a reference or blanking level established by flowing a gas through the chamber whereby the flowing gas exhibits no absorbance in the spectral region of interest with respect to components of the stack gases to be investigated.

Keeping in mind the above considerations, major features of the art pertaining to spectrophotometric determination of the concentration of at least one gas in a plurality of gases, and known to the applicant, will be described briefly in the following:

In U.S. Pat. No. 4,126,396 there is disclosed a method and apparatus for non-dispersive optical determination of gas and smoke components in a mixture of stack gases by reflection and detection of radiation having a different wavelength for each gas component, and wherein the radiation is periodically intercepted before it enters the gas mixture and is reflected back to a photoreceiver. The system uses a rotating filter wheel disposed in front of the photoreceiver to select in succession three different and distinct wavelengths of radiation dedicated to the measurement of smoke components, and of the gas components for the gases $SO_2$ and $NO_2$, respectively. Reference signals are provided at each of the test wavelengths by selectable insertion of a reference reflector in the radiation beam.

In U.S. Pat. No. 3,979,589 there is described a method and system for the infrared analysis of gases which is particularly directed at detecting automobile emissions. In a preferred single path instrument a rotating filter wheel is used between a sample gas cell and a detector to sequentially select a first wavelength at which a gas in the cell appears absorptive, and a second wavelength of infrared radiation at which the gas in the measuring cell appears non-absorptive, thereby establishing a reference signal level. The infrared gas analyzer is calibrated by a zeroing procedure which utilizes ordinary air.

In U.S. Pat. No. 5,053,623 there is disclosed a photometric analyzer for measuring differential total reduced sulfur in a sample gas stream. A sample measuring cell alternately receives a gas sample of $SO_2$ gas from a $SO_2$ sample supply, and a sample of $SO_2$ gas which was converted in an oven from the total reduced sulfur. Additionally, zero air is supplied to the sample cell for measurement by the analyzer of the $SO_2$ levels in the sample gas. The measurements are performed at a single wavelength of radiation of about 300 nm.

In U.S. Pat. No. 4,441,815 there is disclosed a wavelength-modulated derivative spectrometer for continuous measurement of trace amounts of $NH_3$ gas in a stack gas which includes a high concentration of $SO_2$. The system has features which can substantially eliminate interference from the spectrum of $SO_2$ which has a relatively finely structured periodic absorption spectrum so as to enable measurement of small concentrations of $NH_3$ which has a relatively broad structure absorption spectrum. The self-modulating spectrometer has an entrance slit, a dispersion grating, and an exit slit, coupled by suitably disposed reflective elements. Wavelength modulation is provided by periodically scanning the wavelength of light passed out from the exit slit by means for vibrating either the entrance slit or the exit slit or by vibrating other components of the instrument. The above reference also discloses probe means for extracting a gas sample from a stack gas stream, and heated conduit means, as well as a heated measuring cell so as to prevent a possible chemical reaction between the $NH_3$ and the $SO_2$ gas and condensation of water vapor in the sample gas stream.

In U.S. Pat. No. 5,272,345 there is disclosed a calibration method and apparatus for measuring the concentration of components of a fluid, in which for example, the concentration of $NH_3$ gas can be determined spectrophotometrically in the presence of an interfering gas such as sulfur dioxide ($SO_2$) or nitric oxide (NO). The spectrophotometric measurements are determined from an intensity of radiation over a selected range of wavelengths using a peak-to-trough calculation. A reference level is established by measuring the amount of radiation which passes through a non-absorptive zero gas (such as $N_2$), or which alternatively passes through an evacuated measuring chamber. The disclosed apparatus uses an optical grating and a photodiode array detector to generate signals corresponding to radiation passing through the sample gases to be measured, and of signals corresponding to signals of the zero gas or evacuated chamber condition. Referring to an article by Nakabayashi et al, titled "Development of Low Level $NH_3$ Measuring Method," the above disclosure appears to indicate that it is undesirable or unnecessary to maintain certain conduits and the measuring chamber of a stack gas monitoring system at an elevated temperature.

In a European Patent Application No. EP0591758, there is disclosed a multiple component analysis arrangement for detecting gases or liquids, in which a pulsed radiation source is provided to direct ultraviolet radiation pulses to a measuring cell through which the sample gases or liquids are flowing, and providing through a beam-splitting arrangement a reference beam of pulses which is used to determine the stability of the pulsed radiation source. The arrangement uses a spectrophotometer of the type having a diffraction grating for creating a spectral dispersion of light incident thereon and for directing the dispersed light onto a linear photodiode array for simultaneous measurement at a plurality of wavelength. The arrangement relies on establishing a baseline or blank spectrum in which non-absorptive gases such as air or nitrogen are used in the measuring chamber to provide for a baseline calibration of the optical components of the spectrometer. Such baseline calibration data are stored in a storage element of a data processing system associated with the instrument. The above publication suggests the use of a massive quartz rod for coupling radiation out of the radiation source and a separate quartz rod for coupling radiation into an entrance slit of the spectrophotometer. Not suggested in this publication are particular approaches to calibration of the analysis arrangement with respect to the gases or liquids to be analyzed, nor is there any teaching on how to protect the measuring cell and its inlet and outlet conduits from contamination due to deposits arising from the measurement of emission products from stacks of fossil fuel burning facilities.

Thus, while each of the aforementioned publications appears to offer a particular solution to multi-component gas analysis, none of the above approaches appear to incorporate all those features which would be desirable in a stack gas monitor system for real-time spectrophotometric determination of a concentration of a first gas which can be selectably introduced as a measured amount into a stack gas stream of a plurality of stack gases, where the plurality of stack gases would serve as a blanking or reference level in a spectrophotometric system in the absence of the first gas.

SUMMARY OF THE INVENTION

It is the principal object of the present invention to provide an improved stack gas monitor system having an optimized gas flow portion and having a spectrophotometric portion readily attachable thereto for real-time spectrophotometric determination of a concentration of a first gas having a characteristic absorption spectrum and which is selectably introducible as a measured amount into a stack gas stream of a plurality of stack gases.

Another object of the invention is to provide an improved stack gas monitor system having means for purging the gas flow portion with a selected purging gas prior to spectrophotometric determinations.

Another object of the invention is to provide an improved stack gas monitor system having means for calibrating the system with a plurality of measured amounts of the first gas flowing through the gas flow portion in the absence of the stack gases.

A still further object of the invention is to provide an improved stack gas monitor system having means for establishing a stack gas stream blank with a sample of a predetermined amount of the plurality of stack gases flowing through the gas flow portion in the absence of the selectably introducible first gas so as to provide spectrophotometric stack gas blank data for storage in a data file of a data processing member.

A further object of the invention is to provide an improved stack gas monitor system having means for introducing a measured amount of the first gas into the stack gas stream to form a composite gas stream.

A still further object of the present invention is to provide an improved stack gas monitor system having means for verifying the flow of a sample of a predetermined amount of a composite gas stream through the gas flow portion of the system.

Another object of the present invention is to provide an improved stack gas monitor system having means for measuring spectrophotometric composite gas data in the spectrophotometric portion of a composite gas stream sample.

Another object of the invention is to provide an improved stack gas monitor system having means for calculating in real time the absorbance values of a gas having a characteristic absorption spectrum in a composite gas within an ultraviolet spectral range of wavelengths.

A still further object of the invention is to provide an improved stack gas monitor system having means for determining in real time the concentration of a first gas in a composite gas.

Another object of the invention is to provide an improved stack gas monitor system having means for monitoring the concentration of a gas in the stack gas stream of a plurality of stack gases.

Another object of the present invention is to provide an improved stack gas monitor system having a gas flow portion designed to minimize a buildup of deposits on inner surfaces of selected gas flow conduit members and on surfaces of a gas flow chamber resulting from interaction among constituent components of the stack gas or a first gas used in a stack gas process during the flow of a gas sample therethrough.

While all of the foregoing objects are accomplished in a preferred embodiment of the invention, a system which attains only one or more of these objects is within the scope of this invention.

Briefly described, the present invention provides, in accordance with a presently preferred embodiment, a stack gas monitor system for real-time spectrophotometric determination in a spectrophotometric portion of the system of a concentration of a first gas having a characteristic absorption spectrum and which is selectably introducible as a measured amount into a stack gas stream of a plurality of stack gases flowing as a sample gas stream through a gas flow portion of the system with at least a second gas of the stack gas stream having an absorption spectrum extending within an ultraviolet spectral range of wavelengths of radiation and having absorbance values therein which are higher than the absorbance values of the first gas when introduced into the stack gas stream to form a composite gas stream. The system can be calibrated with a plurality of measured amounts of the first gas flowing through the gas flow portion and providing, in response thereto for at least one wavelength within the characteristic spectrum, spectrophotometric calibration data in the spectrophotometric portion for storage in a calibration data file of a data processing member. The system also provides means for establishing a stack gas stream blank with a sample of a predetermined amount of the plurality of stack gases flowing through the gas flow portion in the absence of the first gas, thereby providing in response thereto spectrophotometric stack gas blank data in the spectrophotometric portion for storage in a stack gas blank data file of a data processing member. Upon introduction of measured amount of the first gas into the stack gas stream, a composite stack gas stream is formed and the flow of a sample thereof through the gas flow portion of the system is verified. Spectrophotometric composite gas data are measured in the spectrophotometric portion in response to the verified flow of the composite gas stream sample. Absorbance values of the first gas having the characteristic absorption spectrum in the composite gas are calculated in real time by a data processing member and within the ultraviolet spectral range of wavelengths. The concentration of the first gas in the composite gas is determined in real time, and the concentration of the first gas in the stack gas stream of the plurality of stack gases is monitored.

BRIEF DESCRIPTION OF THE DRAWINGS

The aforementioned and other objects, features and advantages of the present invention will be better understood and appreciated more fully from the following detailed description, taken in conjunction with the accompanying drawings.

DETAILED DESCRIPTION

Figure 1:
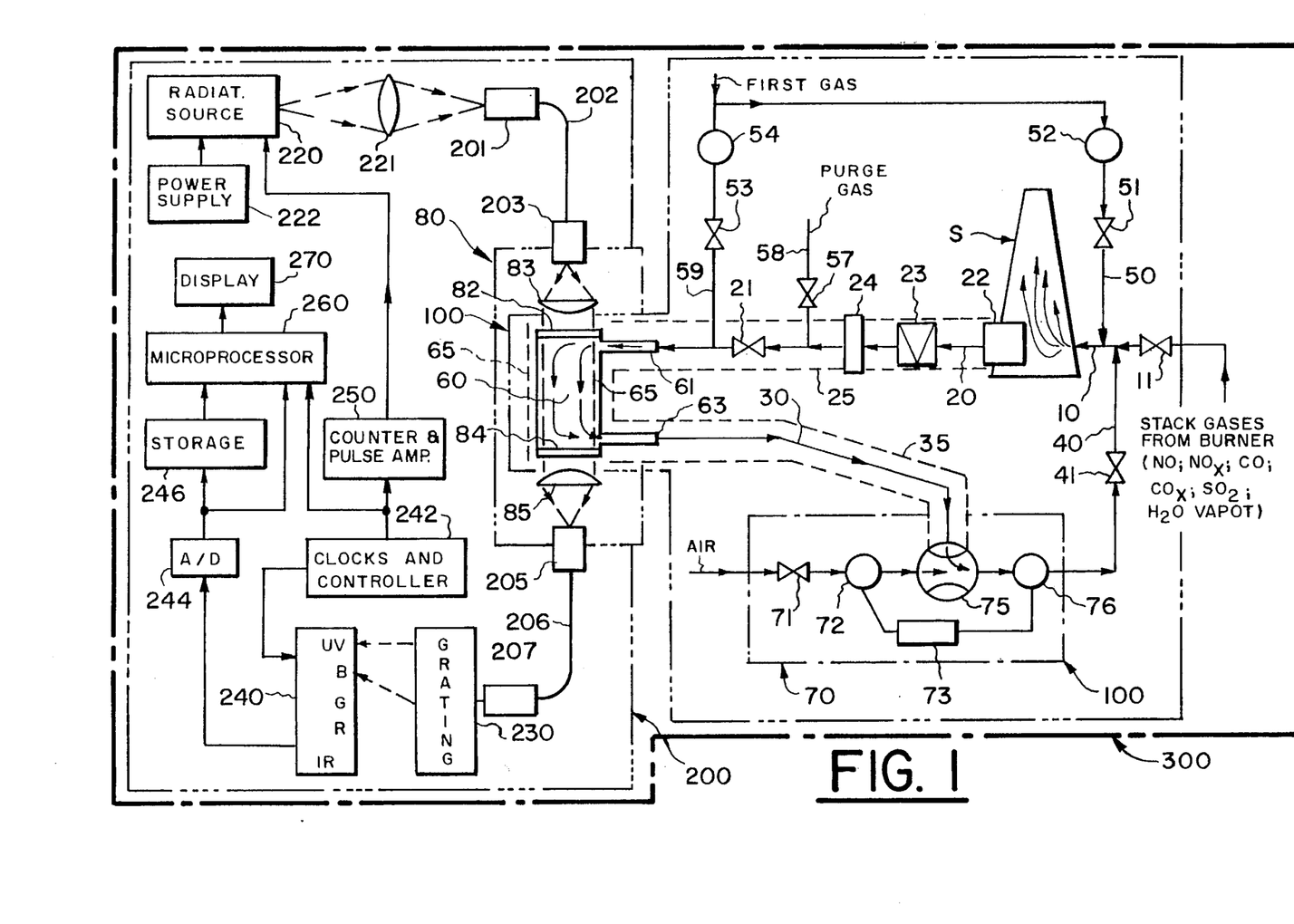
FIG. 1 is a schematic diagram of the stack gas monitor system in accordance with the present invention, indicating a gas flow portion and a spectrophotometric portion which includes data storage members and a microprocessor for calculating absorbance values and for determining first gas concentration levels. Also indicated is a gas flow-through cell assembly and a gas flow monitor assembly.

Referring now to FIG. 1, there is shown a schematic diagram of a stack gas monitor system 300 having a gas flow portion 100 and a spectrophotometric portion 200. A gas flow monitor assembly 70 is indicated as a subportion of the gas flow portion 100. A gas flow compartment 60 of a gas flow-through assembly 80 is formed between a gas inlet port 61 and a gas outlet port 63, the gas flow compartment 60 being defined by an upper wall 82, a lower wall 84, and side walls (not particularly detailed in FIG. 1). The upper and lower walls 82 and 84 of the gas flow compartment 60 are substantially transparent to radiation incident as collimated radiation on the upper wall 82 and provided by a collimating lens assembly 83, and radiation emanating from the lower wall 84 and to be condensed by a condensing lens assembly 85.

Referring first particularly to the gas flow portion 100, stack gases from a burner facility (not shown) are directed to a stack S through a valve means 11 disposed in a first conduit or pipe 10. A stack gas from a coal-fired or from an oil-fired burning facility usually contains a plurality of gases such as NO, CO, $SO_2$, water vapor, and higher oxides of nitrogen and carbon, indicated as $NO_x$ and $CO_x$, respectively. Depending upon the type of fuel used in a burning facility and the prevailing burning conditions, numerous other gas constituents may be found in the stack gas, and the concentrations of the individual gases in the stack gas stream can vary substantially. Stack gases from a burner can have a fairly high temperature, for example a temperature in the range from 270°–320° C.

Due to growing environmental concerns about the adverse environmental impact of emissions from large industrial or commercial burning facilities, it has become necessary to control such emissions, one aspect of control being the transformation of nitrogen oxides (NO, $NO_x$) into environmentally less harmful compounds such as, for example nitrogen gas ($N_2$) and water vapor ($H_2O$). It is well known to bring about such transformation by a chemical reaction between the nitrogen oxide gases and another gas, for example $NH_3$ or the like, with the chemical reaction being particularly effective at the relatively high temperature of the stack gas stream. Accordingly, the present invention contemplates the use of $NH_3$ gas as a chemical reactant.

Returning now to the discussion of the gas flow portion 100, the arrows in the various conduits or pipes of the gas flow portion indicate gas flow therein which would prevail during stack gas monitoring, i.e., under conditions which include a sample flow of the stack gases from the burning facility and the flow of a first gas, for example, $NH_3$, introduced into the first conduit 10 through a fifth conduit 50 as a measured amount through a flow meter 52 and a valve 51 from a first gas ($NH_3$) supply (not shown). A second conduit 20 accepts at a stack end thereof through a probe 22 extending into the stack S a sample of the stack gases, with the sample including constituents of the original stack gases generated in the burning facility, partially transformed constituents of the stack gases by the above chemical reaction with the $NH_3$ first gas, and a trace amount of unreacted $NH_3$ gas. The gas sample flows along conduit 20 through a filter member 23 for removing particulates, an orifice member 24 used for creating a reduction of gas pressure in the second conduit 20 between the orifice member 24 and the gas inlet port 61 of the gas flow-through assembly 80. A valve 21 is disposed along conduit 20 at a location between a purge gas line 58 entering the conduit 20 and having a valve 57, and a first gas calibration line 59 entering the conduit 20 and which is used to provide measured amounts of the first gas ($NH_3$) from the first gas supply (not shown) through a flow meter 54 and a valve 53. The gas sample flow is directed through the gas inlet port 61 into the gas flow compartment 60, and through a gas outlet port 63 thereof via a third gas flow conduit 30 to one inlet port of the flow monitor assembly 70. The flow monitor assembly 70 has a discharge port (not shown) to which a fourth conduit is connected for returning the gas flow sample to the first conduit 10 near its stack end.

The flow monitor assembly 70 uses an air-operated aspirator 75 which has a first aspirator inlet port connected to a flow monitor end of the third conduit 30, and which has a second aspirator inlet port connected through a first flow meter 72 and a valve 71 to a supply (not shown) of pressurized air and having a pressure regulator attached thereto. The flow of air through the aspirator 75 induces and controls the flow of the gas sample through the gas flow portion 100. A second flow meter 76 is used to indicate the sum of the flow of the air and the flow of the stack gas sample. An alarm system 73 may be suitably connected between the flow meters 72 and 76 to provide an alarm signal whenever a difference between the flow indication of the flow meter 76 and the air flow meter 72 decreases below a predetermined value.

In order to prevent or to at least minimize the buildup of deposits due to chemical reactions on inner surfaces of the conduits 20 and 30, as well as on the inner surfaces of the gas flow compartment 60, the conduits 20 and 30 are maintained at an elevated temperature approximating a temperature in the stack S proximate the stack end of the conduit 20 by respective conduit heaters 25 and 35, shown in dashed outline surrounding the conduits 20 and 30. A heating element 65 is indicated schematically in dashed outline as heating the gas flow compartment 60 of the gas flow-through assembly 80 to maintain a temperature therein approximating a temperature in the stack proximate the stack end of the second conduit 20.

During development of a prototype gas portion 100, it was determined that conventional stainless steel conduits used to construct the conduits 20 and 30 appeared to catalyze chemical reactions among some of the constituent gases of the sample gas stream even as these two conduits were maintained at the elevated temperature by the heating members 25 and 35. Accordingly, it has been particularly advantageous to construct conduits 20 and 30 as tubular members which have an inner tubular surface which is chemically inert with respect to such catalytic reactions of stack gases and the first gas flowing therethrough. Such inner tubular surfaces can be provided by a metal alloy which is particularly enriched with metals of nickel and cobalt and having a particular morphology or microstructure. One such metal alloy is commercially available under the designation C-276 Hostalloy.

In summary, the gas flow portion 100 of the stack gas monitor system 300 includes the following major elements: a conduit 10 for delivering a stack gas stream from a burner to the stack S; a conduit 50 for accepting at a stack end thereof a selectably introducible and measured amount of a reactive first gas, for example $NH_3$ gas, to be introduced into the stack gas stream; a conduit 20 for accepting at a stack end thereof a sample of stack gases and the first gas, and for providing the gas sample at a cell assembly end to a gas inlet port 61 of a gas flow-through cell assembly 80 having a gas flow compartment 60; a conduit 30 having a cell assembly end connected to a gas outlet port 63 of the assembly 80 and having a flow monitor end connected to one inlet port of a flow monitor assembly 70; and a conduit 40 having a flow monitor end thereof connected to a discharge port of the flow monitor assembly 70 and having a stack end thereof connected to the conduit 10 for discharging the gas sample flow through the stack S.

Before discussing the operation of the stack gas monitor system 300, the spectrophotometric portion 200 of the system will be described. A radiation source 220 (for example, a xenon lamp) is provided for generating at predetermined intervals pulses of radiation including radiation of wavelengths which extend within an ultraviolet spectral range in which the first gas ($NH_3$) has a characteristic absorption spectrum. The radiation emitted from the source 220 is condensed by a condensing lens 221 onto a first end of a fiber optic coupler 201 which couples the radiation into a fiber optic bundle 202 and through a second fiber optic coupler 203 into the gas flow-through cell assembly 80. A collimating lens 83 disposed within the assembly 80 proximate the gas inlet port 61 provides collimated radiation to be incident on the upper wall 82 of the gas flow compartment 60. A condensing lens disposed within the assembly 80 and proximate the gas outlet port 63 condenses the collimated radiation emanating from the lower wall 84 of the gas flow compartment 60 on a first end of a fiber optic coupler 205 and through a fiber optic bundle 206 to another coupler 207. One end of the fiber optic coupler 207 projects the radiation through a slit (not particularly detailed) onto a holographic grating 230 for spectral dispersion of the radiation over a wavelength range which includes at least the ultraviolet spectral region, but may include other spectral ranges provided by the radiation source, for example a wavelength range extending into a blue (B), green (G), or red (R) spectral regions. Such spectrally dispersed radiation provided by the grating 230 is directed to a radiation detector which is suitably oriented with respect to the entrance slit of the grating 230. Preferably, the radiation detector is a linear photodiode array having a plurality of radiation sensitive photodiodes arranged as a single line, and with each photodiode generating a photodiode signal in response to an intensity level incident thereon from the spectrally dispersed radiation. As is well known in the art of photodiode arrays, the array 240 is operatively controlled by a controller 242 which also provides clock pulses required to clock out sequentially the signals generated in each photodiode of the array 240. These analog photodiode signals are converted into digitized signal levels in an A/D converter 244, the digitized signal levels being either stored in data storage files of a storage member 246, or being directly inputted to a microprocessor 260 used for calculating and determining spectral absorbance values and gas concentration levels of the gases under investigation, as will be described in more detail hereinafter. Such results may be displayed on a display member 270 for the purpose of monitoring the concentration of gas constituents flowing through the gas flow compartment 60 as well as for viewing or printing the absorbance spectra of the gases. Clock signals or derivatives thereof are provided by the controller 242 to another input of the microprocessor 260 to serve as synchronization signals for a video display. Clock signals or derivatives thereof are also provided from the controller 242 to a counter and pulse amplifier 250 which, in turn, provides trigger pulses at predetermined intervals to an input of the radiation source 220, the latter being operated from a power supply 222.

For clarity of presentation, the pathway of radiation through the spectrophotometric portion 200 is indicated in dotted outline. It will be apparent from FIG. 1 that the optical portions of the gas flow-through assembly 80 are common to the spectrophotometric portion 200 of the stack gas monitor system 300, while the gas flow compartment 60 of the assembly 80 is an integral part of the gas flow portion 100 of the system 300.

Figure 2:
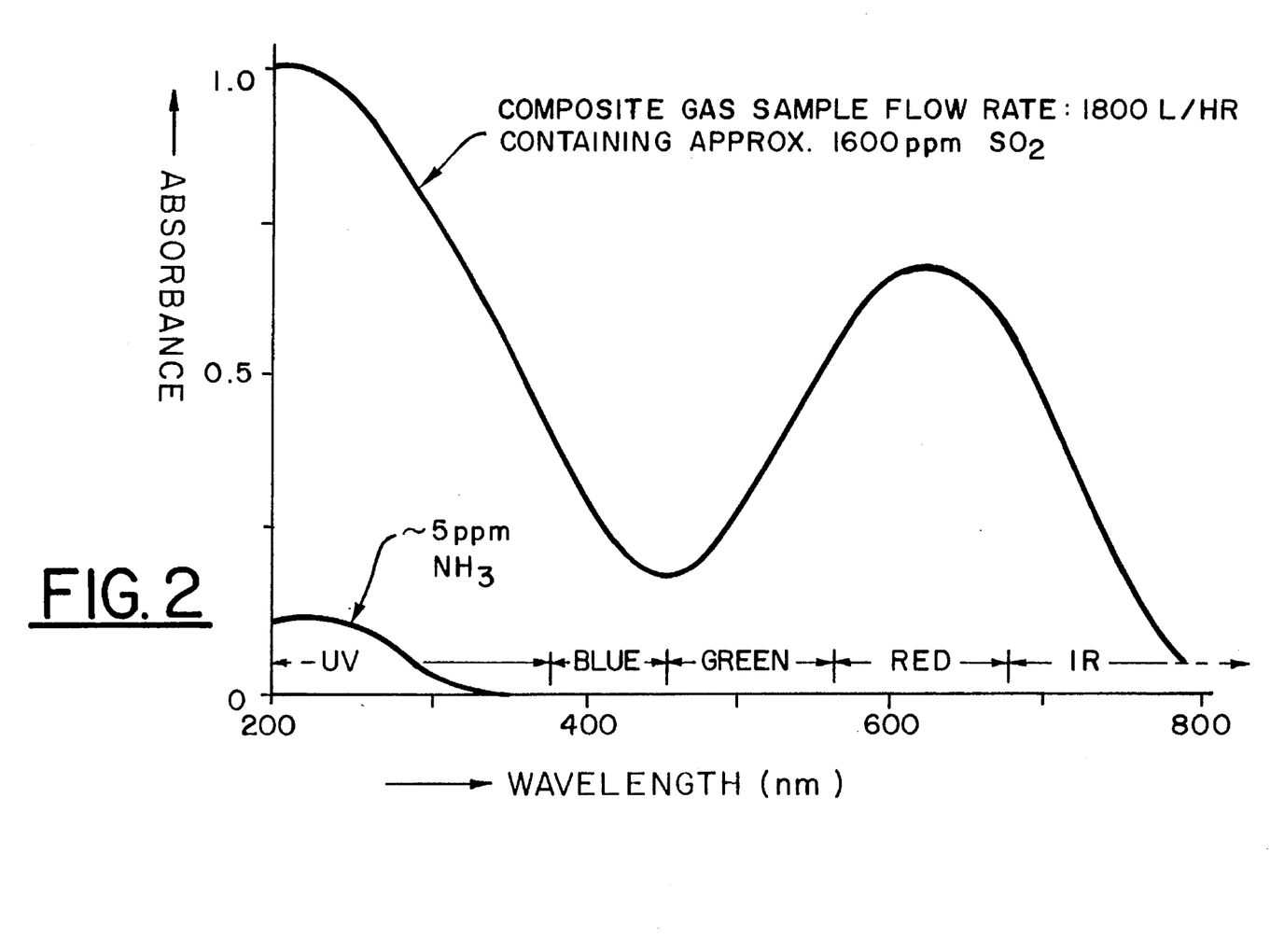
FIG. 2 depicts in an upper trace the spectral absorbance of a composite gas sample flowing through the gas flow portion of the stack gas monitor system at a total flow rate of about 1,800 l/hour and containing about 1,600 ppm of $SO_2$, and shows in a lower trace the spectral absorbance of a first gas $NH_3$ calculated from the composite gas sample of the upper trace and having a concentration determined to be about 5 ppm in the composite gas.
Figure 3:
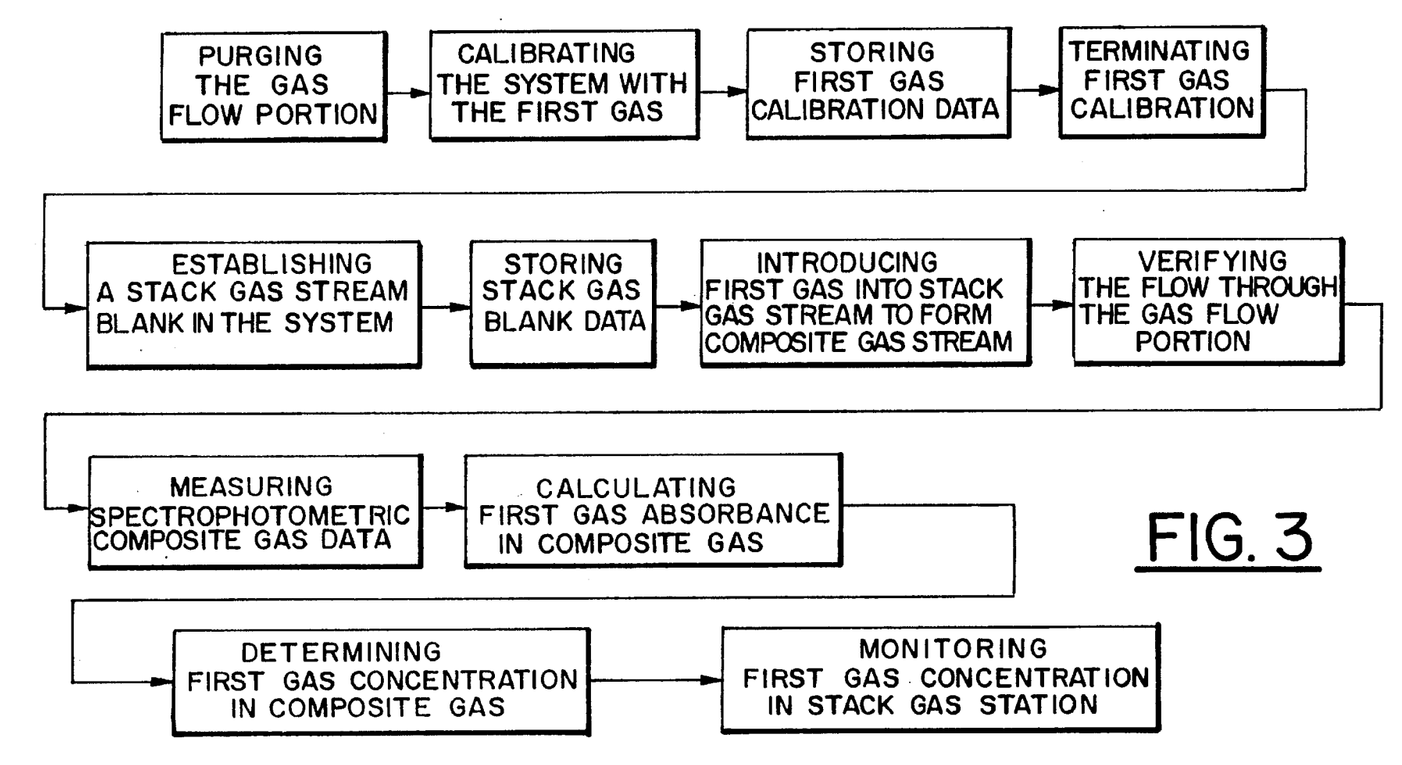
FIG. 3 shows a schematic flow diagram of the sequence of process steps used in the operation of the stack gas monitor system in accordance with the invention.

The operation of the stack gas monitor system can be more readily appreciated in the context of the objects of the present invention by reference to FIG. 2 and FIG. 3.

Since the gas flow portion 100 of the stack monitor system 300 is a permanent installation at a plant site, a spectrophotometric portion 200 can be brought to the plant for conducting a periodic inspection of the plant's stack gas emissions through the stack S. The spectrophotometric portion 200 is readily coupled to the also permanently installed gas flow-through assembly 80 by inserting the fiber optic couplers 203 and 205 therein.

Irrespective of whether or not a sample gas stream had been flowing through the gas flow portion 100 during a time prior to plant emission inspection, the present invention is practiced by first purging the gas flow portion 100 of possible residual gases or of the sample gas stream if it was flowing. The purging is performed by introducing a purge gas into the conduit 20 from a purge gas line 58 by opening a purge valve 57 while leaving valve members 21, 71, 41, and 11 in an open position. Valves 51 and 53 associated with a first gas ($NH_3$) supply are closed during the purging operation. A purge gas may be a gas such as nitrogen or air provided by a suitable purge gas supply (not shown) under controlled flow conditions. The purge gas is directed to flow both toward and through the gas flow compartment 60, as well as in the direction toward the probe 22 via the orifice member 24 and the filter 23 and passing through the probe 22 into the stack S. The purging gas flow through the gas flow compartment 60 is induced and controlled by the flow monitor assembly 70 in a manner similar to the flow monitoring of the stack gas sample. The purging is terminated after an appropriate period of time by closing the purge valve 57.

The now purged gas flow portion 100 is thus prepared for calibrating the stack gas monitor system 300 as follows: With valve member 21 in the conduit 20 in a closed position, a plurality of selected amounts of the first gas ($NH_3$) are sequentially introduced via the flow meter 54 and the now open valve 53 in the calibration line 59 and into the conduit 20, the first gas calibration gas flow being directed through the gas flow compartment, through conduit 30 and through the flow monitor assembly 70 to be discharged through conduit 40 into the stack. The spectrophotometric portion 200 is operative during the system calibration, thereby providing for each one of the plurality of measured amounts of the $NH_3$ calibration gas flow spectrophotometric calibration data which are stored as digitized data levels in a gas calibration data file of storage member 246. The first gas calibration may be performed over substantially the entire wavelength range included in a characteristic absorption spectrum of the $NH_3$ gas, and alternatively signal levels corresponding to at least one particular wavelength within the characteristic absorption spectrum may be stored in the calibration data file. The calibration may be performed by mixing the known measured amounts of the NH$_3$ gas with a carrier gas (not shown in FIG. 1), with the carrier gas serving as a diluent gas for the NH$_3$, and being non-absorptive within the spectral range of wavelength of the NH$_3$ characteristic absorption spectrum.

From the plurality of measured amounts of the first gas flowing through a part of the gas flow portion during the first gas calibration of the system, the data stored in the calibration data file of storage member 246 provide essentially a first gas calibration curve relating the photodiode array signal levels to concentration levels of the first gas flowing through the gas flow compartment 60 of the assembly 80. Upon completion of the first gas calibration, the calibration valve 53 is closed and the valve 21 in conduit 20 is opened. It will be appreciated that the first gas calibration need only to be performed once in any particular installation of a stack gas monitor system, providing that no unusual operating conditions of the facility occur during a period of operation prior to a next scheduled inspection of the stack gas emissions.

With valve 51 in the conduit 50 closed, a stack gas sample comprising the plurality of stack gases is now extracted from the stack S by the probe 22 to flow through the gas flow portion 100 of the system. This stack gas sample flow in the absence of the first gas (NH$_3$) is referred to as a stack gas stream blank which generates in the photodiode array 240 of the spectrophotometric portion 200 stack gas blank signal levels which are stored as spectrophotometric stack gas blank data in a stack gas blank data file of the storage member 246.

Valve member 51 in conduit 50 is now opened and a measured amount of the NH$_3$ first gas flow is introduced into the stack gas stream through the flow meter 52, thereby forming a composite gas stream which includes some of the constituents of the stack gases coming from the burner, some constituents reflective of at least partially transformed nitrogen oxides (for example, some N$_2$ and additional water vapor), as well as a desired unreacted amount of the NH$_3$ first gas. The gas flow of this composite gas through the gas flow portion 100 is verified in the flow monitor assembly 70. Of course, if the stack gas blank establishing procedure has been performed just prior to the formation of the composite gas sample stream, gas sample flow verification can be omitted as a dedicated process step at this time.

Once the flow of the composite gas sample through the gas flow portion 100 has stabilized, the spectrophotometric portion 200 is actuated by generating the pulsed radiation in the radiation source 220, thereby passing the radiation through the gas flow compartment 60 and providing in the photodiode array 240 signal levels which correspond to the composite gas sample. Digitized signal levels representative of the composite gas sample flow are inputted directly into one input of the microprocessor 260 in which absorbance values are calculated for the first gas (NH$_3$) in the composite sample gas stream, whereby the absorbance values are computed at each one of a predetermined number of wavelengths within the characteristic absorption spectrum of the first gas in accordance with the following relationship:

$$A(\lambda) = \log \frac{S_{blank}(\lambda)}{S_{comp}(\lambda)}$$

where $A(\lambda)$ is the absorbance value at a particular wavelength $\lambda$ within said characteristic first gas absorption spectrum;

$S_{blank}(\lambda)$ is the signal level corresponding to said stack gas stream blank at the particular wavelength $\lambda$, stored in said stack gas blank data file $S_{comp}(\lambda)$ is the signal level corresponding to said measured composite gas at the particular wavelength $\lambda$, measured in said composite gas stream sample log denotes the logarithm.

It will be appreciated that a predetermined number of discrete wavelengths within the characteristic absorption spectrum of the first gas can be a number selected to cover the entire wavelength range corresponding to the characteristic absorption spectrum, or it can be a reduced number at which such absorbance values are calculated.

The microprocessor 260 then determines in the first gas concentration level in the composite gas sample at at least one wavelength within the first gas characteristic absorption spectrum from the first gas calibration data stored in the calibration data file and from the just computed first gas absorbance value at the same wavelength. Again, it will be apparent that a first gas concentration in the composite gas stream sample can be computed by incorporating data corresponding to signals gathered at more than one wavelength within the characteristic absorption spectrum.

Referring now to FIG. 2, there is shown in an upper trace the spectral absorbance of a composite gas sample containing about 1,600 ppm of SO$_2$ flowing through the gas flow portion 100 of the stack gas monitor system 300 at a total flow rate of about 1,800 l/hour, and indicating in a lower trace the spectral absorbance of a NH$_3$ first gas, the absorbance of which was calculated by the microprocessor 260 from the composite gas sample of the upper trace, and having a first gas concentration determined therefrom to be about 5 ppm in the composite gas. For illustrative purposes only, various wavelength ranges along the wavelength axis of FIG. 2 are indicated as "UV", "BLUE", "GREEN", "RED", and "IR" (infrared). These designations of commonly accepted spectral ranges over a wavelength range extending from about 200 nm to about 800 nm, are also indicated in abbreviated form in the outline of the photodiode array detector 240 in the spectrophotometric portion 200 of FIG. 1, where it is shown schematically by the dotted lines extending between the grating 230 and the detector 240 that the wavelength range of primary interest extends within an ultraviolet (UV) spectral region commensurate with the characteristic absorption spectrum of the first gas NH$_3$.

It is apparent from FIG. 2 that the absorbance values of the composite gas sample (including the approximately 5 ppm of NH$_3$) has absorbance values ranging from about 0.8 absorbance units to about 1.0 absorbance units within a portion of the ultraviolet spectral range where the 5 ppm NH$_3$ concentration level contained in the composite gas sample at the indicated total flow rate has a calculated absorbance value in the range of about 0.08 to about 0.10 within the portion of the ultraviolet spectral range. A significant fraction of the absorbance of the composite gas sample at the indicated flow rate is due to the concentration level of about 1,600 ppm of the SO$_2$ gas constituent in the composite stack gas sample.

It has been found that a preferred range of absorbance values is from about 0.8 to about 1.2 at a second gas (SO$_2$) concentration of about 1,600 ppm in the stack gas stream, with this preferred absorbance range of values prevailing through a portion of the ultraviolet spectral range of wavelength extending from about 200 nm to about 250 nm, while the absorbance values of the first gas (NH$_3$) when introduced into the stack gas stream are in a preferred range of from about 0.08 to about 0.1 over this portion of the ultraviolet spectral range of wavelength at a first gas concentration of about 5 ppm in the stack gas sample stream, where the respective absorbance value ranges are obtained at a total sample gas flow rate of about 1,800 l/hour. A preferred total sample gas flow rate of sample gas flowing through the gas flow portion 100 of the stack gas monitor system 300 is in the range from about 1,200 to about 2,400 l/hour.

From the foregoing description of the preferred embodiment, it will be apparent that a stack gas monitor system and method have been provided for determining in real-time in a spectrophotometric portion a concentration of a first gas having a characteristic absorption spectrum and which is selectably introducible as a measured amount into a stack gas stream of a plurality of stack gases flowing as a sample gas stream through a gas flow portion with at least a second gas of the stack gas stream having an absorption spectrum extending within an ultraviolet spectral range of wavelengths of radiation and having absorbance values therein which are higher than absorbance values of the first gas when introduced into the stack gas stream to form a composite gas stream.

The gas flow portion of the system is optimized as a permanent installation in a fossil-fuel burning facility to include means for purging the gas flow portion, means for introducing into the gas flow portion a plurality of measured amounts of the first gas as a calibration gas, means for establishing a stack gas stream blank in the gas flow portion, means for introducing a measured amount of the first gas into the stack gas stream so as to form the composite gas stream, and means for verifying the flow of a sample of the composite gas stream through the gas flow portion.

The spectrophotometric portion of the system can be readily attached to the gas flow portion, and it includes means for providing spectrophotometric first gas calibration data, means for providing spectrophotometric stack gas blank data, means for measuring spectrophotometric composite gas data, means for calculating in real time the absorbance values of the first gas having the characteristic absorption spectrum in the composite gas, means for determining in real time the concentration of the first gas in the composite gas, and means for monitoring the concentration of the first gas in the stack gas stream.

Various modifications and arrangements will undoubtedly suggest themselves to those skilled in the art of gas flow systems and to those skilled in the art of spectrophotometric gas flow analysis. Such modifications and alternative arrangements are within the spirit and scope of the present invention, as defined in the specification and the claims.

What is claimed is:

1. A stack gas monitor system for real-time spectrophotometric determination in a spectrophotometric portion of said system of a concentration of a first gas having a characteristic absorption spectrum and which is selectably introducible as a measured amount into a stack gas stream of a plurality of stack gases flowing as a sample gas stream through a gas flow portion of said system with at least a second gas of said stack gas stream having an absorption spectrum extending within an ultraviolet spectral range of wavelengths of radiation and having absorbance values therein which are higher than absorbance values of said first gas when introduced into said stack gas stream to form a composite gas stream, said system comprising:

means for calibrating the system with a plurality of measured amounts of said first gas flowing through said gas flow portion and providing in response thereto for at least one wavelength within said characteristic absorption spectrum spectrophotometric calibration data in said spectrophotometric portion for storage in a calibration data file of a data processing member associated with said spectrophotometric portion of said system, thereby providing a first gas concentration calibration;

means for terminating the calibration with said first gas;

means for establishing a stack gas stream blank in said system with a sample of a predetermined amount of said plurality of stack gases flowing through said gas flow portion and providing in response thereto spectrophotometric stack gas blank data in said spectrophotometric portion for storage in a stack gas blank data file of said data processing member;

means for introducing a measured amount of said first gas into said stack gas stream, thereby forming said composite gas stream;

means for verifying the flow of a sample of a predetermined amount of said composite gas stream through said gas flow portion;

means for measuring spectrophotometric composite gas data in said spectrophotometric portion in response to said verified flow of said composite gas stream sample;

means for calculating the absorbance values of said first gas having said characteristic absorption spectrum in said composite gas within said ultraviolet spectral range of wavelengths;

means for determining the concentration of said first gas in said composite gas; and means for monitoring said concentration of said first gas in said stack gas stream of said plurality of stack gases.

2. The stack gas monitor system of claim 1, wherein said gas flow portion comprises:

a first conduit for supplying said stack gas stream from a burner and said selectably introducible first gas from a first gas supply to said stack;

a second conduit for accepting at a stack end thereof a sample of said plurality of stack gases and said selectably introducible first gas and for providing said gases at a cell assembly end thereof;

a gas flow-through cell assembly having a gas inlet port connected to the cell assembly end of said second conduit means and having a gas outlet port and forming a gas flow compartment therebetween, said cell assembly including means for coupling radiation of wavelengths extending through an ultraviolet spectral range into said compartment proximate said gas inlet port and means for coupling radiation out of said compartment proximate said gas outlet port;

a third conduit having a cell assembly end connected to said gas outlet port and having a flow monitor end;

a flow monitor assembly having one inlet port connected to said flow monitor end of said third conduit means and having a flow monitor discharge port;

a fourth conduit having a flow monitor end thereof connected to said flow monitor discharge port and having a stack end thereof connected to said stack for discharge therethrough; and a fifth conduit for accepting at a first gas accepting end thereof said first gas from a first gas supply and having a first conduit end thereof connected to said first conduit said fifth conduit including a selectably activatable valve and selectably controllable flow control means for selectably introducing said measured amount of said first gas into said stack gas stream.

3. The stack gas monitor system of claim 2, wherein said second conduit means comprises:

a tubular member having an inner tubular surface which is chemically inert with respect to catalytic reactions of said stack gases and said first gas flowing therethrough; and means for maintaining said tubular member at an elevated temperature approximating a temperature in said stack proximate said stack end of said second conduit means.

4. The stack gas monitor system of claim 3, wherein said second conduit further comprises:

probe means connected at said stack end and extending into the stack for extracting said sample of said plurality of stack gases and said selectably introducible first gas therefrom;

filter means for filtering particulates from the gases;

orifice means for creating a reduction of gas pressure in said second conduit means between said orifice means and said cell assembly end thereof;

purge means for introducing said purge gas for initial purging of said second conduit said gas flow compartment, said third conduit said flow monitor assembly, and said fourth conduit prior to accepting said sample of said plurality of stack gases at said stack and;

gas calibration means for providing said measured amounts of said first gas to flow through said gas flow compartment following said introduction of said purge gas and prior to providing said plurality of stack gases at said cell assembly end; and a valve for shutting off said plurality of stack gases during actuation of said gas calibration means.

5. The stack gas monitor system of claim 3, wherein said gas flow-through cell assembly comprises:

means for maintaining said gas flow compartment at an elevated temperature approximating a temperature in said stack proximate said stack end of said second conduit means;

a first lens for coupling radiation into said compartment proximate said gas inlet port; and a second lens for coupling said radiation out of said compartment proximate said gas outlet port.

6. The stack gas monitor system of claim 5, wherein said third conduit means comprises:

a tubular member having an inner tubular surface which is chemically inert with respect to catalytic reactions of said stack gases and said first gas flowing therethrough; and means for maintaining said tubular member at an elevated temperature approximating a temperature in said stack proximate said stack end of said second conduit means.

7. The stack gas monitor system of claim 2, wherein said flow monitor assembly comprises:

an aspirator member having a first aspirator inlet port connected to said flow monitor end of said third conduit means, having a second aspirator inlet port connected through a first flow meter to a supply of pressurized air, and having an aspirator outlet port connected through a second flow meter to said flow monitor discharge port, said first flow meter providing an indication of flow of said air from said supply of air and said second flow meter providing an indication of a sum of the flow of said stack gases and the flow of said air.

8. The stack gas monitor system of claim 7, wherein said flow monitor assembly further comprises:

alarm means for providing an alarm signal whenever a difference between the flow indication of said second flow meter and the flow indication of said first flow meter decreases below a predetermined value.

9. The stack gas monitor system of claim 2, wherein said spectrophotometric portion comprises:

means for generating at predetermined intervals pulses of radiation including radiation of wavelengths extending within said ultraviolet spectral range;

a first condensing lens for condensing said generated radiation;

a first fiber optic for accepting said condensed radiation at a first coupler end thereof and for coupling said condensed radiation into said gas flow-through cell assembly at a second coupler end;

a collimating lens disposed within said assembly and proximate said gas inlet port of said gas flow compartment for providing collimated radiation incident on an upper wall of said gas flow compartment proximate said gas inlet port;

a second condensing lens disposed within said assembly and proximate said gas outlet port of said gas flow compartment for condensing said collimated radiation emanating from a lower wall of said gas flow compartment proximate said gas outlet port;

a second fiber optic for accepting said condensed radiation provided by said second condensing lens means at a first coupler end thereof and for coupling said radiation out at a second coupler end thereof;

a spectrophotometer having an entrance slit, a holographic grating for spectral dispersion of radiation incident on said entrance slit and provided thereon at said second coupler end of said second fiber optic means, and a linear photodiode array oriented with respect to said entrance slit, said photodiode array having a plurality of radiation sensitive photodiodes arranged as a single line with each photodiode generating a photodiode signal in response to an intensity level incident thereon from said spectrally dispersed radiation;

means for operatively controlling the photodiode array including means for providing clock pulses therefor;

means for deriving from said clock pulses and synchronized therewith trigger pulses for actuating the generation of said pulses of radiation at said predetermined intervals;

means for converting said photodiode signals into digitized signal levels;

means for storing said digitized signal levels corresponding to said calibration data and said stack gas blank data in said calibration data file and in said stack gas blank data file, respectively, of said data processing member; and microprocessor means for calculating in real time said absorbance values of said first gas in said composite gas and for computing said concentration of said first gas in said composite gas.

10. The stack gas monitor system of claim 3, wherein said means for maintaining said tubular member of said second conduit means at an elevated temperature is a heater member capable of maintaining a temperature of about 300° C.

11. The stack gas monitor system of claim 5, wherein said means for maintaining said gas flow compartment at an elevated temperature is a heater member capable of maintaining a temperature of about 300° C.

12. The stack gas monitor system of claim 6, wherein said means for maintaining said tubular member of said third conduit at an elevated temperature is a heater member capable of maintaining a temperature of about 300° C.

13. The stack gas monitor system of claim 3, wherein said inner tubular surface is a surface of a metal alloy, said alloy substantially comprising metals selected from the group consisting of nickel and cobalt.

14. The stack gas monitor system of claim 6, wherein said inner tubular surface is a surface of a metal alloy, said alloy substantially comprising metals selected from the group consisting of nickel and cobalt.

15. The stack gas monitor system of claim 1, wherein said first gas is ammonia ($NH_3$) and said second gas of said plurality of stack gases of said stack gas stream is sulfur dioxide ($SO_2$).

16. The stack gas monitor system of claim 1, wherein said sample gas stream flowing through said gas flow portion has a flow rate in the range of from 1200 to 2400 liter/hour.

17. The stack gas monitor system of claim 1, wherein said absorbance values within a portion of said ultraviolet spectral range of wavelengths of said second gas ($SO_2$) are in a range of from about 0.8 to about 1.2 at a second gas concentration of about 1600 parts per million (ppm) in said stack gas stream, and said absorbance values within said portion of said ultraviolet spectral range of said first gas ($NH_3$) when introduced into said stack gas stream are in a range of from about 0.08 to about 0.1 at a first gas concentration of about 5 ppm in said stack gas sample stream, said respective absorbance value ranges prevailing at a total sample gas flow rate of about 1800 liter/hour.

18. A stack gas monitor method of real-time spectrophotometric determination in a spectrophotometric portion of a monitor system of a concentration of a first gas having a characteristic absorption spectrum and which is selectably introducible as a measured amount into a stack gas stream of a plurality of stack gases flowing as a sample gas stream through a gas flow portion of said system with at least a second gas of said stack gas stream having an absorption spectrum extending within an ultraviolet spectral range of wavelengths of radiation and having absorbance values therein which are higher than absorbance values of said first gas when introduced into said stack gas stream to form a composite gas stream, said method comprising the steps of:

calibrating the system with a plurality of measured amounts of said first gas flowing through said gas flow portion and providing in response thereto for at least one wavelength within said characteristic absorption spectrum spectrophotometric calibration data in said spectrophotometric portion for storage in a calibration data file of a data processing member associated with said spectrophotometric portion of said system, thereby providing a first gas concentration calibration;

terminating the calibration with said first gas; establishing a stack gas stream blank in said system with a sample of a predetermined amount of said plurality of stack gases flowing through said gas flow portion and providing in response thereto spectrophotometric stack gas blank data in said spectrophotometric portion for storage in a stack gas blank data file of said data processing member;

introducing a measured amount of said first gas into said stack gas stream, thereby forming said composite gas stream;

verifying the flow of a sample of a predetermined amount of said composite gas stream through said gas flow portion;

measuring spectrophotometric composite gas data in said spectrophotometric portion in response to said verified flow of said composite gas stream sample;

calculating in real time the absorbance values of said first gas having said characteristic absorption spectrum in said composite gas within said ultraviolet spectral range of wavelengths;

determining in real time the concentration of said first gas in said composite gas; and monitoring said concentration of said first gas in said stack gas stream of said plurality of stack gases.

19. The stack gas monitor method of claim 18, further comprising the steps of:

supplying said stack gas stream from a burner and said selectably introducible first gas from a first gas supply to said stack;

accepting a sample of said plurality of stack gases and said selectably introducible first gas and providing said gases to a cell where said spectrophotometric measuring step is carried out;

firstly flowing said gases through said cell;

secondly flowing said gases through a flow monitor having a flow monitor discharge port; and selectably introducing said measured amount of said first gas into said stack gas stream.

20. The stack gas monitor method of claim 19, wherein said first flowing step is carried out via a conduit which is chemically inert with respect to catalytic reactions of said stack gases and said first gas flowing therethrough; and further comprising the steps of:

maintaining said conduit at an elevated temperature approximating a temperature of the gases flowing into the conduit from the stack in said stack;

maintaining an elevated temperature of approximating said temperature in said cell assembly and wherein;

said second flowing step is carried out at said temperature.

21. The stack gas monitor method of claim 18, further including the steps of:

extracting said sample of said plurality of stack gases and said selectably introducible first gas through a probe in the stack gas stream extending into the stack;

filtering particulates from the gases extracted by the probe;

flowing the filtered gases to a cell where said spectrophotometric measuring step is carried out while reducing the pressure of the gases reaching said cell;

initially purging the monitor system with a purge gas prior to accepting said sample of said plurality of stack gases;

calibrating said measured amounts of said first gas flowing through said cell following said purging step and prior to providing said sample to said cell; and shutting off by said stream of stack gases during said calibrating step.

22. The stack gas monitor method of claim 18, wherein said calibrating step further comprises the step of:

mixing a carrier gas with said measured amounts of said first gas, said carrier gas being substantially non-absorbing within said ultraviolet spectral range of wavelength and being inert with respect to said first gas.

23. The stack gas monitor method of claim 18, wherein said absorbance values calculating step comprises the step of:

computing said absorbance values at each one of a predetermined number of wavelengths within said characteristic absorption spectrum of said first gas in accordance with the following relationship, $$A(\lambda) = \log \frac{S_{blank}(\lambda)}{S_{comp}(\lambda)}$$

where $A(\lambda)$ is the absorbance value at a particular wavelength $\lambda$ within said characteristic first gas absorption spectrum;

$S_{blank}(\lambda)$ is the signal level corresponding to said stack gas stream blank at the particular wavelength $\lambda$, stored in said stack gas blank data file $S_{comp}(\lambda)$ is the signal level corresponding to said measured composite gas at the particular wavelength $\lambda$, measured in said composite gas stream sample log denotes the logarithm.

24. The stack gas monitor method of claim 23, wherein said first gas concentration determining step includes the step of:

computing said concentration of said first gas in said composite gas at said at least one wavelength from said first gas concentration calibration and from the absorbance value at the same wavelength calculated in said computing step.

* * * * *